US010556001B2

(12) United States Patent
Jiang et al.

(10) Patent No.: US 10,556,001 B2
(45) Date of Patent: *Feb. 11, 2020

(54) THERMAL INACTIVATION OF ROTAVIRUS

(71) Applicant: The United States of America, as represented by the Secretary, Department of Health and Human Services, Bethesda, MD (US)

(72) Inventors: Baoming Jiang, Atlanta, GA (US); Roger I. Glass, Atlanta, GA (US); Jean-Francois Saluzzo, La-Gaude (FR)

(73) Assignee: The united States of America, as represented by the Secretary, Department of Health and Human Services, Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/725,221

(22) Filed: Oct. 4, 2017

(65) Prior Publication Data

US 2018/0028644 A1    Feb. 1, 2018

Related U.S. Application Data

(63) Continuation of application No. 13/718,648, filed on Dec. 18, 2012, now abandoned, which is a continuation of application No. 12/676,490, filed as application No. PCT/US2008/075239 on Sep. 4, 2008, now Pat. No. 8,357,525.

(60) Provisional application No. 60/969,826, filed on Sep. 4, 2007.

(51) Int. Cl.
*A61K 39/15*    (2006.01)
*A61K 39/12*    (2006.01)
*A61K 39/00*    (2006.01)

(52) U.S. Cl.
CPC .............. *A61K 39/15* (2013.01); *A61K 39/12* (2013.01); *A61K 2039/5252* (2013.01); *A61K 2039/545* (2013.01); *A61K 2039/55505* (2013.01); *A61K 2039/575* (2013.01); *C12N 2720/12334* (2013.01)

(58) Field of Classification Search
None
See application file for complete search history.

(56) References Cited

U.S. PATENT DOCUMENTS

| | | | |
|---|---|---|---|
| 4,341,763 A | 7/1982 | Zygraich | |
| 4,608,254 A | 8/1986 | Philapitsch et al. | |
| 5,605,692 A | 2/1997 | Thomas et al. | |
| 5,610,049 A | 3/1997 | Clark | |
| 6,110,724 A | 8/2000 | Nakagomi et al. | |
| 6,607,732 B2 | 8/2003 | Morein et al. | |
| 6,780,630 B1 | 8/2004 | Estes et al. | |
| 8,822,192 B2 * | 9/2014 | Jiang | A61K 39/15 435/236 |
| 9,974,851 B2 * | 5/2018 | Jiang | A61K 39/15 |
| 2002/0058043 A1 | 5/2002 | Hoshino et al. | |
| 2002/0127317 A1 | 9/2002 | Hotchkiss et al. | |
| 2002/0155128 A1 | 10/2002 | Knape et al. | |
| 2003/0092145 A1 | 5/2003 | Jira et al. | |

FOREIGN PATENT DOCUMENTS

| | | |
|---|---|---|
| WO | WO 1991/011194 | 8/1991 |
| WO | WO 1999/062346 | 12/1999 |
| WO | WO 2002/062382 | 8/2002 |
| WO | WO 2004/026336 | 4/2004 |

OTHER PUBLICATIONS

Ward et al., "Why does the world need another rotavirus vaccine?" *Therapeutics and Clinical Risk Management* 4(1): 49-63 (Feb. 2008).
Bruce et al., "Recognition of rotavirus antigens by mouse L3T4-positive T helper cells," *Journal of General Virology* 75(8): 1859-1866 (Aug. 1, 1994).
Crawford et al., "Characterization of virus-like particles produced by the expression of rotavirus capsid proteins in insect cells," *Journal of Virology* 68(9): 5945-5952 (Sep. 1, 1994).
Estes et al., "Rotavirus stability and inactivation," *Journal of General Virology* 43: 403-409 (1979).
Jiang et al., "Immunogenicity of a thermally inactivated rotavirus vaccine in mice," *Human Vaccines* 4(2): 143-147 (Mar. 1, 2008).
Lytle et al., "Predicted inactivation of viruses of relevance to biodefei se by solar radiation," *Journal of Virology* 79(22): 14244-14252 (Nov. 15, 2005).
Martin et al., "Ionic strength-and temperature-induced K(Ca) shifts in the uncoating reaction of rotavirus strains RF and SA11: correlation with membrane permeabilization" *Journal of Virology* 76(2): 552-559 (Jan. 15, 2002).
McKimm-Breschkin et al., "Conditions required for induction of interferon by rotaviruses and for their sensitivity to its action," *Infection and Immunity* 36(3): 857-863 (Jun. 1, 1986).
Meng et al., "Physiochemical stability and inactivation of human and simian rotaviruses," *Applied and Environmental Microbiology* 53(4): 727-730 (Apr. 1, 1987).
Moe et al., "The effects of relative humidity and temperature on the survival of human rotavirus in faeces." *Archives of Virology* 72(3): 179-186 (Sep. 1, 1982).

(Continued)

*Primary Examiner* — Stacy B Chen
(74) *Attorney, Agent, or Firm* — Klarquist Sparkman, LLP

(57) ABSTRACT

Methods of thermally inactivating a rotavirus are provided according to the present invention which include exposing the rotavirus to a temperature in the range of about 50° C.-80° C., inclusive, for an incubation time sufficient to render the rotavirus incapable of replication or infection. The thermally inactivated rotavirus is antigenic and retains a substantially intact rotavirus particle structure. Vaccine compositions and methods of vaccinating a subject against rotavirus are provided which include generation and use of thermally inactivated rotavirus.

17 Claims, 13 Drawing Sheets

(56) References Cited

OTHER PUBLICATIONS

Offit and Dudzik, "Noninfectious rotavirus (Strain RRV) induces an immune response in mice which protects against rotavirus challenge," *Journal of Clinical Microbiology* 25(5): 885-888 (May 1989).

Pontes et al., "Pressure-induced formation of inactive triple-shelled rotavirus particles is associated with changes in the spike protein Vp4," *Journal of Molecular Biology* 307(5): 1171-1179 (Apr. 13, 2001).

Rodgers et al., "Morphological response of human rotavirus to ultra-violet radiation, heat, and disinfectants," *Journal of Medical Microbiology* 20(1): 123-130 (Aug. 1, 1985).

Spillmann et al., "Inactivation of animal viruses during sewage sludge treatment," *Applied and Environmental Microbiology* 53(9): 2077-2081 (Sep. 1, 1987).

Walker et al., "Proteolytic inactivation of simian-11 rotavirus: a pilot study," *Veterinary Microbiology* 74(3): 195-206 (Jun. 1, 2000) (Abstract Only).

Ward et al., "Discovery of an agent in wastewater sludge that reduces the heat required to inactivate reovirus," *Applied and Environmental Microbiology* 34(6): 681-688 (Dec. 1, 1977).

Ward et al., "Identification of detergents as components of wastewater sludge that modify the thermal stability of reovirus and enteroviruses," *Applied and Environmental Microbiology* 36(6): 889-897 (Dec. 1, 1978).

Ward et al., "Effects of wastewater sludge and its detergents on the stability of a rotavirus," *Applied and Environmental Microbiology* 39(6): 1154-1158 (Jun. 1, 1980).

McNeal et al., "Stimulation of local immunity and protection in mice by intramuscular immunization with triple- or double-layered rotavirus particles and QS-21," *Virology* 243(1): 158-166 (Mar. 30, 1998).

\* cited by examiner

Inactivation of vaccine human rotavirus strain CDC-9

Live
FIG. 5A

Killed
FIG. 5B

Analysis of IRV CDC-9 by SDS-PAGE and Western blot

37°C 10 min    97°C 5 min          37°C 10 min    97°C 5 min 1   live 2   killed 3   live 4   killed 5          1   live 2   killed 3   live 4   killed 5

THERMAL INACTIVATION OF ROTAVIRUS

CROSS REFERENCE TO RELATED APPLICATIONS

This application is a continuation of U.S. patent application Ser. No. 13/718,648, filed Dec. 18, 2012, which is a continuation of U.S. patent application Ser. No. 12/676,490, filed Mar. 4, 2010, issued as U.S. Pat. No. 8,357,525, which is a U.S. National Stage of International Application No. PCT/US2008/075239, filed Sep. 4, 2008, which claims the benefit of U.S. Provisional Patent Application No. 60/969,826, filed Sep. 4, 2007. All of the prior applications are incorporated herein by reference.

FIELD

The present invention relates generally to rotavirus compositions and methods. More specifically the present invention relates to methods of thermally inactivating rotavirus and inactivated rotavirus vaccine compositions.

BACKGROUND

Of the various enteric pathogenic viruses causing severe diarrhea in children, rotavirus is the most common causing an average of 611,000 deaths per year. Virtually all children are infected by rotavirus by age 5. The virus is believed to be highly contagious and has been described as a "democratic" virus since the infection affects no particular socio-economic or geographic group disproportionately. While the majority of children having access to adequate supportive and palliative medical care survive infection with no significant long-term consequences, the number of deaths associated with severe diarrhea, vomiting, dehydration and shock is unacceptable and requires preventative intervention if possible.

Vaccination against rotavirus-mediated disease is one strategy for addressing this significant health problem. Currently, although live, oral vaccines have been developed and licensed, continuing safety and efficacy concerns justify an alternative approach to parenteral vaccination with an inactivated rotavirus vaccine. There is a dearth of effective methods for inactivating rotavirus and vaccine compositions including inactivated rotavirus. A particular difficulty is treatment of live rotavirus to inactivate the virus while maintaining antigenicity associated with substantially intact double-layer and triple-layer rotavirus particles.

There is a continuing need for methods of inactivating rotavirus and compositions including inactivated rotavirus.

SUMMARY

Vaccine compositions are provided according to embodiments of the present invention which include antigenic thermally inactivated rotavirus characterized by a substantially intact triple-layered rotavirus particle structure. A vaccine composition optionally includes an adjuvant, such as AlOH. Further optionally, a vaccine composition of the present invention is formulated for parenteral administration to a subject. A thermally-inactivated rotavirus included in a vaccine composition of the present invention is any human or animal rotavirus including any of group A, B, C, D, E, F and G rotaviruses.

Methods of vaccinating a subject against rotavirus according to embodiments of the present invention include administering a therapeutically effective amount of a vaccine composition which includes antigenic thermally inactivated rotavirus to the subject. The thermally inactivated rotavirus is characterized by a substantially intact rotavirus particle structure.

A method of vaccinating a subject against rotavirus according to the present invention includes administration to a mammalian or avian subject. In particular embodiments, the subject is human. A method of vaccinating a subject against rotavirus according to the present invention includes administration of thermally-inactivated human or animal rotavirus including any of group A, B, C, D, E, F and G rotaviruses.

Administration of a vaccine composition including thermally inactivated rotavirus to vaccinate a subject against rotavirus is accomplished by any suitable route. In particular embodiments, the vaccine composition is administered to the subject by a parenteral route.

A method of vaccinating a subject against rotavirus according to embodiments of the present invention includes administering at least two doses of the vaccine composition to the subject.

A method of inactivating a rotavirus, particularly for use in vaccinating a subject, is provided according to embodiments of the present invention. Particular methods include suspending isolated rotavirus particles in an aqueous buffer, the aqueous buffer having an osmolality in the range of about 200-500 mOsm, comprising a concentration of at least one salt of a divalent cation in the range of about 1 mM-15 mM, and an amount of a sugar and/or sugar alcohol in the range of about 1-20% w/v to produce a starting preparation of rotavirus particles having an intact rotavirus particle structure. The starting preparation of rotavirus particles is exposed to a temperature in the range of about 50° C.-80° C., inclusive, for an incubation time sufficient to render the rotavirus incapable of replication or infection, thereby producing a heat-inactivated rotavirus preparation that is antigenic and substantially retains the intact rotavirus particle structure of the starting preparation.

The starting preparation of rotavirus particles can be double-layer rotavirus particles, triple-layer rotavirus particles, or a mixture of double-layer rotavirus particles and triple-layer rotavirus particles.

The incubation time is in the range of about 10 minutes-24 hours, inclusive. Optionally, the incubation time is in the range of about 30 minutes-10 hours, inclusive and in particular embodiments, the incubation time is in the range of about 1-3 hours, inclusive.

In a further option, the isolated rotavirus particles are filtered prior to exposing the starting preparation of rotavirus particles to a temperature in the range of about 50° C.-80° C., inclusive.

In particular embodiments of inventive methods, the starting preparation of rotavirus particles is exposed to a temperature in the range of about 55° C.-70° C. for an incubation time as described. In preferred embodiments, the starting preparation of rotavirus particles is exposed to a temperature in the range of about 58° C.-67° C., inclusive for an incubation time as described.

Optionally, heat-inactivation of rotavirus includes a first incubation period and a second incubation period in which the starting preparation of rotavirus particles is exposed to a temperature in the range of about 50° C.-80° C., inclusive. In such an embodiment, the first incubation period and the second incubation period combined are in the range of about 10 minutes-24 hours, inclusive.

A heat-inactivated rotavirus preparation substantially retains the intact rotavirus particle structure of the starting preparation and the heat-inactivated rotavirus preparation is characterized by an amount of substantially intact viral proteins VP1, VP2 and VP6 which is substantially similar to an amount of substantially intact viral proteins VP1, VP2 and VP6 present in the starting preparation. Where the starting preparation includes triple-layer rotavirus particles, the heat-inactivated rotavirus preparation is characterized by an amount of substantially intact viral proteins VP1, VP2, VP4, VP5, VP6 and VP7 which is substantially similar to an amount of substantially intact viral proteins VP1, VP2, VP4, VP5, VP6 and VP7 present in the starting preparation.

A method of inactivating a rotavirus according to the present invention is applicable to rotaviruses illustratively including human rotaviruses, simian rotaviruses, bovine, lapine, porcine, equine, canine, caprine, avian and murine rotaviruses. Further, a method of inactivating a rotavirus according to the present invention is applicable to rotaviruses illustratively including rotaviruses of group A, B, C, D, E, F and G.

BRIEF DESCRIPTION OF THE DRAWINGS

FIG. 5A is a reproduction of an electron micrograph of a purified human live rotavirus;

FIG. 5B is a reproduction of an electron micrograph of a purified heat-killed human rotavirus having substantially the same morphology as the starting preparation, a sample of which is shown in FIG. 5A;

FIG. 6A is a reproduction of a digitized image of a Coomassie blue stained polyacrylamide gel showing molecular mass markers (kilodaltons) in Lane 1, proteins isolated from live rotavirus in Lanes 2 and 4 and proteins isolated from thermally inactivated rotaviruses in Lanes 3 and 5;

FIG. 6B is a reproduction of a digitized image of an immunoblot showing molecular mass markers (kilodaltons) in Lane 1, mouse anti-rotavirus immunoreactive protein VP5 isolated from live rotaviruses in Lane 2 and mouse anti-rotavirus immunoreactive proteins VP5 or its aggregates isolated from thermally inactivated rotaviruses in Lane 3;

FIG. 7 is a graph showing results of enzyme immunoassay (EIA) for VP5 in live rotavirus (TLPorg) and heat-killed rotavirus (60C2h) indicating that both preparations contain similar levels of VP5 protein;

DETAILED DESCRIPTION

Figure 1A:
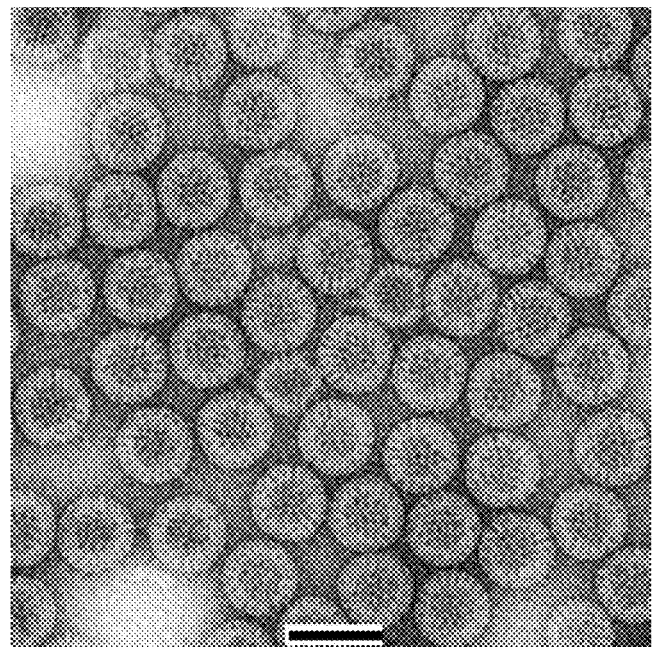
FIG. 1A is a reproduction of an electron micrograph of a purified live simian rotavirus stained with phosphotungstic acid and characterized by a triple-layered structure.
Figure 1B:
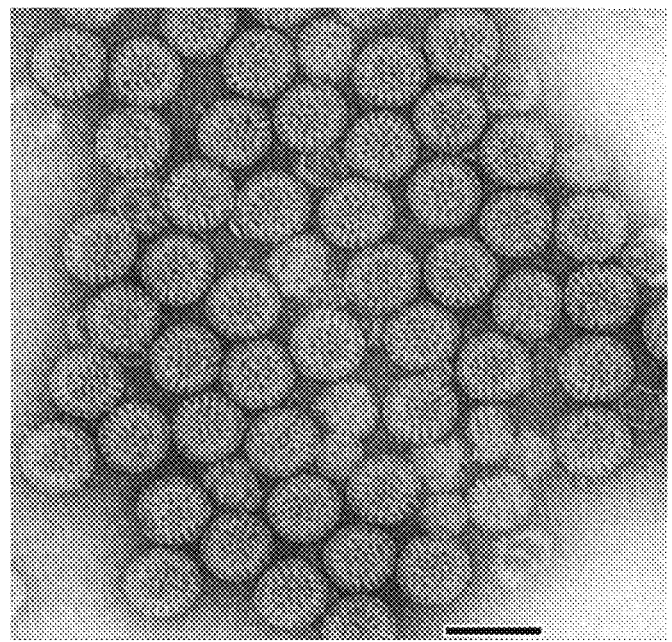
FIG. 1B is a reproduction of an electron micrograph of simian rotavirus particles thermally inactivated according to an embodiment of a method of the present invention stained with phosphotungstic acid and characterized by a triple-layered structure.
Figures 2A, 2B:
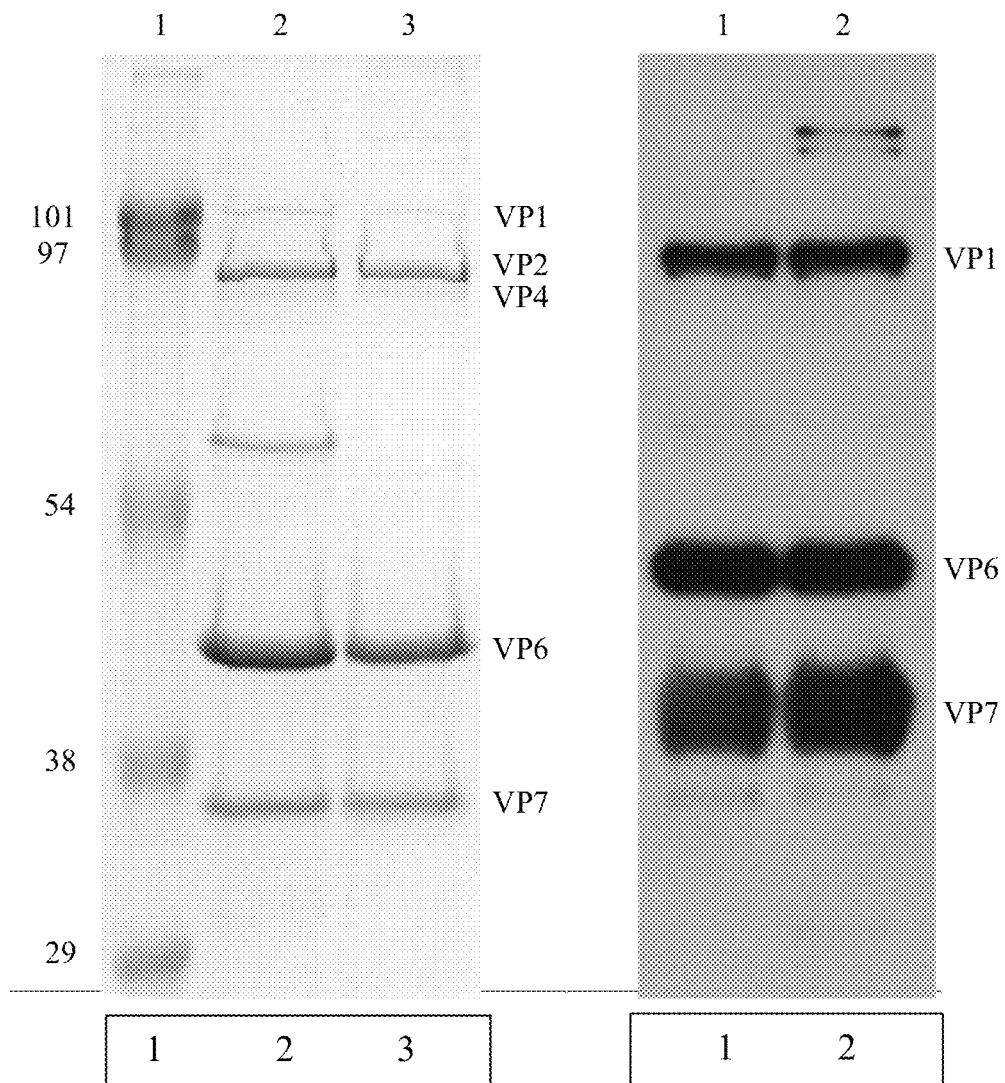
FIG. 2A is a reproduction of a digitized image of a Coomassie blue stained polyacrylamide gel showing molecular mass markers (kilodaltons) in Lane 1, proteins isolated from live rotavirus in Lane 2 and proteins isolated from thermally inactivated rotaviruses in Lane 3.
FIG. 2B is a reproduction of a digitized image of an immunoblot showing rabbit anti-rotavirus immunoreactive proteins isolated from live rotaviruses in Lane 1 and rabbit anti-rotavirus immunoreactive proteins isolated from thermally inactivated rotaviruses in Lane 2.

Methods of thermally inactivating rotavirus and vaccine compositions including thermally inactivated rotavirus are provided according to the present invention.

Broadly described, a combination of the temperature at which rotavirus particles are heated and the time of incubation of the rotavirus at that temperature is selected to effectively to render rotavirus inactive while maintaining rotavirus antigenicity and retaining a substantially intact rotavirus particle structure according to a method of the present invention.

The terms "killed rotavirus" "inactive rotavirus" and "inactivated rotavirus" refer to rotavirus which is thermally treated and incapable of replication or infection under conditions in which live rotavirus can replicate and/or infect a cell.

Rotavirus particle structure is well-known in the art. The term "triple-layer" refers to rotavirus particles having three concentric capsid layers. The term "double-layer" refers to rotavirus particles missing the outermost capsid layer and retaining the middle and innermost capsid layers.

The term "antigenic" refers to a material that elicits an immune response in a subject and particularly a protective immune response.

A method of inactivating a rotavirus includes exposing the rotavirus to a temperature in the range of about 50° C.-80° C., inclusive, for an incubation time sufficient to render the rotavirus inactive while maintaining rotavirus antigenicity and retaining a substantially intact rotavirus particle structure.

In further embodiments, a method of inactivating a rotavirus includes exposing the rotavirus to a temperature in the range of about 55° C.-70° C., inclusive, for an incubation time sufficient to render the rotavirus inactive while maintaining rotavirus antigenicity and retaining a substantially intact rotavirus particle structure.

In a particular embodiment, a method of inactivating a rotavirus includes exposing the rotavirus to a temperature in the range of about 58° C.-67° C., inclusive, for an incubation time sufficient to render the rotavirus inactive. The inactivated rotavirus is antigenic and retains a substantially intact rotavirus particle structure.

The incubation time during which the rotavirus is exposed to a selected temperature is in the range of about 10 minutes-24 hours, inclusive.

In further embodiments of methods according to the present invention, incubation time during which the rotavirus is exposed to a selected temperature is in the range of about 30 minutes-10 hours, inclusive.

In still further embodiments of methods according to the present invention, incubation time during which the rotavirus is exposed to a selected temperature is in the range of about 1-3 hours, inclusive.

A method of inactivating a rotavirus according to the present invention is applicable to rotaviruses illustratively including human rotaviruses, simian rotaviruses, bovine, lapine, porcine, equine, canine, caprine, avian and murine rotaviruses. Further, a method of inactivating a rotavirus according to the present invention is applicable to rotaviruses illustratively including rotaviruses of group A, B, C, D, E, F and G.

Rotaviruses inactivated by a method of the present invention retain characteristics of live rotaviruses. In particular, where triple-layered rotaviruses are inactivated by incubation at a selected temperature for a selected period of time, the inactivated rotavirus particles retain a substantially intact triple-layered rotavirus particle structure. Double-layered rotaviruses are inactivated by incubation at a selected temperature for a selected period of time, and the inactivated rotavirus particles retain a substantially intact double-layered rotavirus particle structure.

A starting preparation of rotavirus particles to be heat-inactivated optionally includes both double-layer and triple-layer rotavirus particles. Following heat inactivation, the resulting preparation of heat-inactivated rotavirus particles contains a substantially similar proportion of double-layer and triple-layer rotavirus particles as the starting preparation.

Further, rotaviruses inactivated by a method of the present invention are substantially similar to live rotaviruses with respect to viral protein amount and integrity. In particular, rotaviruses thermally inactivated according to embodiments of methods of the present invention retain an amount of one or more substantially intact viral proteins present in live rotavirus.

For example, a preparation heat-inactivated rotavirus produced according to methods of the present invention is characterized by an amount of substantially intact viral proteins VP1, VP2, VP4, VP5, VP6 and VP7 which is substantially similar to an amount of substantially intact viral proteins VP1, VP2, VP4, VP5, VP6 and VP7 present in the starting preparation. Thus, where a starting preparation of rotaviruses including triple-layered rotaviruses, and which may also include double-layered rotaviruses, is inactivated by a method of the present invention, the resulting preparation of heat-inactivated rotavirus particles retain an amount of substantially intact VP1, VP2, VP4, VP5, VP6 and VP7 proteins which is substantially similar to an amount of substantially intact viral proteins VP1, VP2, VP4, VP5, VP6 and VP7 present in live rotavirus.

Filtration of rotavirus particles is preferably performed prior to heating the rotavirus particles to inactivate the particles. In a preferred option, rotavirus particles are filtered using a filter having a pore size in the range of about 0.2 to 0.8 micron. Without wishing to be bound by theoretical considerations, it is believed that filtration reduces or eliminates rotavirus particle aggregates, allowing more effective thermal inactivation.

Agitation of the particles during incubation, such as by stirring, is advantageous for evenly distributing heat to the rotavirus particles in particular embodiments of inventive methods of rotavirus inactivation.

In particular embodiments of the present invention, rotavirus particles are disposed in a first container during a first portion of the incubation time and the rotavirus particles are transferred to a second container for a second portion of the incubation time.

A starting preparation of rotavirus for heat-inactivation according to methods of the present invention is prepared by standard methods. For example, generally a compatible cell type is inoculated with rotaviruses and the cells are maintained under conditions which allow for viral replication and production of infectious particles.

A particular example of a cell type which permits rotavirus infection, replication and particle production is a mammalian cell line such as a Vero cell line.

The term "isolated rotavirus particles" refers to rotavirus particles that have been separated from the environment in which they are typically found, such as organisms, cells, cultured cell supernatant and waste material such as fecal material or sewage. Rotavirus particles are harvested, typically from cell culture supernatant, for thermal inactivation. The rotavirus particles may be isolated from the cell culture supernatant, for example by filtration and/or centrifugation.

In a particular example, isolated rotaviruses are resuspended in a diluent buffer and exposed to a temperature in the range of about 50° C.-80° C., inclusive, for an incubation time sufficient to render the rotavirus inactive.

A diluent buffer for suspending isolated rotavirus particles is an aqueous buffer, particularly an aqueous buffer that maintains a pH in the range of about pH 5-9 such as, but not limited to, a phosphate buffer, Tris buffer, citrate buffer, borate buffer, glycine buffer, acetate buffer, succinate buffer, HEPES buffer, maleate buffer, PIPES buffer, MOPS buffer, MOPSO buffer or histidine buffer.

In preferred embodiments, a diluent buffer used in methods of the present invention has an osmolality in the range of about 200-500 mOsm, preferably about 225-450 mOsm, and more preferably about 250-350 mOsm.

Included in a diluent buffer is at least one salt of a divalent cation including, but are not limited to, $CaCl_2$, $MgCl_2$ and $MgSO_4$. A salt of at least one divalent cation is included in the diluent buffer in the range of about 1 mM-15 mM.

A virus particle stabilizer is preferably included in the diluent buffer. In particular embodiments, a virus particle stabilizer is a sugar, such as a monosaccharide and/or disaccharide, or sugar alcohol. One or more sugars and/or sugar alcohols is included in the diluent buffer to achieve a total concentration of the sugars and/or sugar alcohols in the range of about 1-20% w/v. Illustrative sugars and sugar alcohols include, but are not limited to, sorbitol, mannitol, glycerol, glucose, sucrose, lactose, maltose and trehalose.

In certain embodiments, a diluent buffer used in a rotavirus thermal-inactivation method is substantially free of amino acids. In further embodiments, a diluent buffer used in a rotavirus thermal-inactivation method is substantially free of vitamins optionally, a diluent buffer used in a rotavirus thermal-inactivation method is substantially free of both amino acids and vitamins.

In embodiments of the present invention, a diluent buffer used in a rotavirus thermal-inactivation method contains $NaHCO_3$ in the range of about 200-2000 mg/L. In further embodiments, a diluent buffer used in a rotavirus thermal-inactivation method contains $NaHCO_3$ in the range of about 300-500 mg/L.

In a particular example, a diluent buffer is Hank's Balanced Salt Solution (HBSS) with 1.3 mM $CaCl_2$, 0.5 mM $MgCl_2$, and 0.4 mM $MgSO_4$, supplemented with 10% sorbitol.

Following inactivation, the isolated rotavirus particles are optionally lyophilized, such as for later resuspension in a pharmaceutically acceptable carrier.

Vaccine compositions are provided according to embodiments of the present invention which include antigenic thermally inactivated rotavirus characterized by a substantially intact triple-layer rotavirus particle structure. In further embodiments, vaccine compositions are provided according to embodiments of the present invention which include both substantially intact triple-layer rotavirus particle structure and substantially intact double-layer rotavirus particle structure.

The term "vaccine composition" is used herein to refer to a composition including a thermally inactivated rotavirus capable of inducing an immune response in a subject inoculated with the vaccine composition. In a particular embodiment, a vaccine composition including a thermally inactivated rotavirus stimulates generation of neutralizing antibodies against the thermally inactivated rotavirus. A vaccine composition preferably includes a pharmaceutically acceptable carrier.

The term "pharmaceutically acceptable carrier" refers to a carrier which is substantially non-toxic to a subject and substantially inert to the thermally inactivated rotavirus included in a vaccine composition. A pharmaceutically acceptable carrier is a solid, liquid or gel in form and is typically sterile and pyrogen free.

A vaccine composition of the present invention may be in any form suitable for administration to a subject.

A vaccine composition is administered by any suitable route of administration including oral and parenteral such as intradermal, intramuscular, mucosal, nasal, or subcutaneous routes of administration.

In preferred embodiments, a vaccine composition of the present invention is administered by a parenteral route. A vaccine composition for parenteral administration may be formulated as an injectable liquid including thermally inactivated rotavirus and a pharmaceutically acceptable carrier. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

A solid dosage form for administration or for suspension in a liquid prior to administration illustratively includes capsules, tablets, powders, and granules. In such solid dosage forms, a rotavirus is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include thermally inactivated rotavirus and a pharmaceutically acceptable carrier formulated as an emulsion, solution, suspension, syrup, or elixir. A liquid dosage form of a vaccine composition of the present invention may include a wetting agent, an emulsifying agent, a suspending agent, a sweetener, a flavoring, or a perfuming agent.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 20th ed., 2003; and J. G. Hardman et al., Goodman & Gilman's The Pharmacological Basis of Therapeutics, McGraw-Hill Professional, 10th ed., 2001.

An adjuvant is optionally included in a vaccine composition according to embodiments of the present invention. The term "adjuvant" as used herein refers to a material which enhances an immune response to an antigen in a subject without substantial adverse reaction. Adjuvants are known in the art and illustratively include Freund's adjuvant, aluminum hydroxide, aluminum phosphate, aluminum oxide, iron oxide, saponin, dextrans such as DEAE-dextran, vegetable oils such as peanut oil, olive oil, and/or vitamin E acetate, mineral oil, bacterial lipopolysaccharides, peptidoglycans, and proteoglycans.

Methods of vaccinating a subject against rotavirus are provided according to embodiments of the present invention which include administering a therapeutic amount of a vaccine composition including antigenic thermally inactivated rotavirus characterized by a substantially intact triple-layered and/or double-layered rotavirus particle structure.

The phrase "therapeutically effective amount" is used herein to refer to an amount effective to induce an immunological response and confers protective immunity to prevent or ameliorate signs or symptoms of a rotavirus-mediated disease. Induction of a protective immunological response in a subject can be determined by any of various techniques known in the art, illustratively including detection of anti-rotavirus antibodies, measurement of anti-rotavirus antibody titer and/or lymphocyte proliferation assay. Signs and symptoms of rotavirus-mediated disease may be monitored to detect induction of an immunological response to administration of a vaccine composition of the present invention in a subject. For example, induction of an immunological response is detected by reduction of clinical signs and symptoms of rotavirus-mediated disease such as reduction of the amount of virus shed in feces, reduction of the number of days on which virus is shed in feces, reduction in the number of days the subject has diarrhea, reduction in mortality, reduction in morbidity, reduction in weight loss or weight gain.

Administration of a vaccine composition according to a method of the present invention includes administration of one or more doses of a vaccine composition to a subject at one time in particular embodiments. Alternatively, two or more doses of a vaccine composition are administered at time intervals. A suitable schedule for administration of vaccine composition doses depends on several factors including age and health status of the subject, type of vaccine composition used and route of administration, for example. One of skill in the art is able to readily determine a dose and schedule of administration to be administered to a particular subject.

A method of vaccinating a subject against rotavirus according to embodiments of the present invention includes administering at least two doses of the vaccine composition to the subject.

While the term "subject" is primarily used herein to refer to a human, it is appreciated that non-human animals, illustratively including cows, horses, sheep, goats, pigs, dogs, cats, birds, poultry, and rodents, are vaccinated according to particular embodiments of the present invention. Thus, a method of vaccinating a subject against rotavirus according to the present invention includes administration to a mammalian or avian subject. In particular embodiments, the subject is human.

Embodiments of inventive compositions and methods are illustrated in the following examples. These examples are provided for illustrative purposes and are not considered limitations on the scope of inventive compositions and methods.

EXAMPLES

Example 1

Vero cells are cultured in Dulbecco's Modified Eagle Medium supplemented with 5% fetal bovine serum (both from Invitrogen Corporation, Grand Island, N.Y.) and 50 micrograms/ml of neomycin (Sigma, St. Louis, Mo.). Confluent monolayers of Vero cells in roller bottles are infected with simian rotavirus YK-1 at a multiplicity of infection of 0.1. YK-1 is a recently isolated rotavirus strain with P[3],G3 specificity, as described in Virol. J., 3:40, 2006. Infected cultures are harvested at 4 days postinfection.

Example 2

Triple-layered rotavirus particles are purified from supernatants by centrifugation through 40% sucrose cushions in TNC buffer (10 mM Tris [pH 8.0], 140 mM NaCl, 10 mM $CaCl_2$) for 2 hrs at 106,750 g using an SW32Ti rotor and then through isopycnic centrifugations in CsCl gradients for 17 hrs at 111,160 g using an SW40Ti rotor. Purified virus particles are resuspended in diluent buffer, Hank's Balanced Salt Solution (HBSS) with 1.3 mM $CaCl_2$, 0.5 mM $MgCl_2$, and 0.4 mM $MgSO_4$, supplemented with 10% sorbitol, for heat inactivation.

Example 3

Purified virus particles are resuspended in Hanks Balanced Salt Solution (HBSS) with $CaCl_2$ and $MgCl_2$ (Invitrogen) supplemented with 10% sorbitol (Sigma) and stored at −70° C. before being inactivated and injected into a subject.

Purified triple-layered rotavirus particles are diluted to a concentration of 300 micrograms/ml with diluent buffer and sterilized by filtration using a Millex®-HV PVDF Syringe driven filter unit (0.45 micron; Millipore Corporation, Bedford, Mass.). To inactivate rotavirus by heat, virus particles in 3.6 ml cryotubes (NalgeNunc, Rochester, N.Y.) are incubated for 1 hr at 60° C. in a waterbath with re-circulating water (model NesLab Ex10; Thermo Electron Corporation, Newington, N.H.) and then transferred to another fresh tube and incubated for an additional 1 hr at 60° C. A small aliquot is immediately tested for any residual infectivity and the remainder is stored at −70° C. before use in the immunization of a subject.

Example 4

The effectiveness of inactivation is examined by inoculating thermally treated rotavirus suspension onto monolayers of Vero cells in roller tubes and incubating in a rolling apparatus at 37° C. for 7 days. Infected cell cultures are then subjected to a second round of amplification in Vero cells in the same manner for another 7 days. YK-1 rotavirus is considered inactivated if inoculated cell cultures tested negative for rotavirus by using a commercial EIA kit (Rotaclone®; Meridian, Cincinnati, Ohio). In controls, non-heat treated YK-1 is inoculated onto Vero cells in the same manner and infected cultures tested positive for rotavirus.

Example 5

The integrity of the rotavirus particles before and after thermal inactivation is determined by electron microscopy. YK-1 rotavirus is purified from infected Vero cell cultures and only triple-layered particles are used for the inactivation study. Live and inactivated triple-layered YK-1 particles are stained with phosphotungstic acid and examined with an electron microscope. After thermal treatment at 60° C. for 2 hrs, YK-1 particles are found to maintain biophysical integrity, as evidenced by the preservation of triple-layered structures that are morphologically similar to live native virions. A reproduction of an electron micrograph of purified live YK-1 rotavirus stained with phosphotungstic acid is shown in FIG. 1A. A reproduction of an electron micrograph of purified heat inactivated YK-1 rotavirus stained with phosphotungstic acid is shown in FIG. 1B. The scale bar shown in both FIGS. 1A and 1B indicates a length of 100 nm.

Example 6

The purity and protein composition of rotavirus particles inactivated by a thermal inactivation method of the present invention are determined by SDS-polyacrylamide gel eletrophoresis and then Coomasie blue staining or Western blot analysis using rotavirus-specific rabbit hyperimmune serum. YK-1 rotavirus is purified from infected Vero cell cultures and only triple-layered particles are used for the inactivation study. After thermal treatment at 60° C. for 2 hrs, heat inactivated YK-1 particles are analyzed by SDS-polyacrylamide gel eletrophoresis and Coomasie blue staining or Western blot analysis using rotavirus-specific rabbit hyperimmune serum. Inactivation of rotavirus in heat-treated samples is confirmed by the lack of virus growth following two sequential passages in Vero cells. In controls, robust virus growth is observed in cells infected with the original live, non heat-treated YK-1 rotavirus. For this analysis, the protein concentration of purified particles is measured by the Bradford method using bovine IgG as standards (Bio-Rad, Hercules, Calif.). Live and thermally inactivated triple-layered rotavirus particles are analyzed on a 12% polyacrylamide gel followed by Coomassie blue staining. This analysis shows that thermally inactivated virus particles contained all major structural viral proteins—VP1, VP2, VP4, VP6, and VP7, and are antigenic, as demonstrated by their detection in Western blot analysis using rabbit hyperimmune serum to RRV rotavirus as shown in FIGS. 2A and 2B. FIG. 2A shows a reproduction of a digitized image of a Coomassie blue stained polyacrylamide gel where Lane 1 contains molecular mass markers (kilodaltons) and Lanes 2 and 3 contain live and killed YK-1, respectively. FIG. 2B shows a reproduction of a digitized image of an immunoblot showing antigenicity of major rotaviral proteins using rotavirus-specific rabbit hyperimmune serum. Lane 1 contains proteins from live YK-1 and Lane 2 contains proteins from killed YK-1. Major structural viral proteins are indicated by labels on the right of FIGS. 2A and 2B.

Example 7

Female inbred BALB/C mice (Covance Research Products, Denver, Pa.) are pre-bled and tested negative for total rotavirus-specific antibody (IgA, IgG and IgM) by EIA. Mice in groups of 7 are immunized I.M. twice with 20 micrograms or 2 micrograms of killed YK-1 in diluent buffer and boosted 21 days later. For controls, mice in group of 6 are immunized with the buffer in the same manner. For immunization, mice are injected with 100 microliters of the vaccine or buffer into a hind leg, bled on days 0, 21, and 35, and exsanguinated on day 49.

Total serum antibody and neutralizing antibody responses to thermally inactivated rotavirus are determined in mice. Mice are vaccinated intramuscularly (I.M.) twice with heat-killed YK-1 and rotavirus-specific total (IgA, IgG, and IgM) and neutralizing antibodies are determined by EIA. For total antibody, each serum specimen is tested at an initial dilution of 1:100. Pre-bleed serum specimens had no detectable antibody at this dilution, a value of 20 is used for determining geometric mean titers and illustration. Neutralizing antibody is tested at an initial dilution of 1:20.

Rotavirus-specific antibodies (IgM, IgG, and IgA) in the sera are measured by an immunoassay with modifications as described in detail in Jiang B, et al., Vaccine 1999; 17:1005-13. Briefly, 96-well plates (NalgeNunc, Rochester, N.Y.) are coated with diluted rabbit hyperimmune serum to RRV rotavirus, incubated with supernatants of RRV-infected MA104 cells, and followed by addition of serially diluted mouse sera. Plates are incubated with horseradish peroxidase (HRP)-conjugated goat anti-mouse IgA, IgG, and IgM antibodies (Kirkegaard and Perry, Gaithersburg, Md.) and then with the substrate tetramethyl benzidine (Aldrich, Milwaukee, Wis.). The reaction is stopped with 1 N HCl and optimal density (OD) at 450 nm is measured with an EIA reader (MRX Revelation, Dynex Technologies, Chantilly, Va.). Antibody titer in a serum is defined as the reciprocal of the highest dilution with a net OD value (OD with RRV minus OD with 5% blotto) of greater than 0.1.

Rotavirus neutralizing antibody is measured by a microneutralization assay as described in detail in Jiang B, et al., Vaccine 1999; 17:1005-13. Mouse sera are serially diluted two-fold in duplicate wells and incubated with trypsin-activated RRV rotavirus. Activated rotavirus or similarly treated serum-free MEM medium is incubated in the absence of sera and served as positive and negative controls, respectively. MA104 cells in MEM medium supplemented with a final concentration of 10 micrograms/ml trypsin and 0.5% chick serum (Invitrogen) are added to each well. After incubation at 37° C. for 18 hrs, plates are fixed with formalin. Rotavirus antigens in MA104 cells are detected by incubating plates with rabbit anti-RRV hyperimmune serum, HRP-labeled anti-rabbit IgG, and then tetramethyl benzidine. Neutralizing antibody titer in a serum is defined as the reciprocal of the highest dilution giving a 70% reduction in absorbance value compared to that in the virus control.

Results shown in FIGS. 3A and 3B indicate that the thermally inactivated rotavirus is highly immunogenic as demonstrated by innoculation of mice with thermally inactivated rotavirus.

Figure 3A:
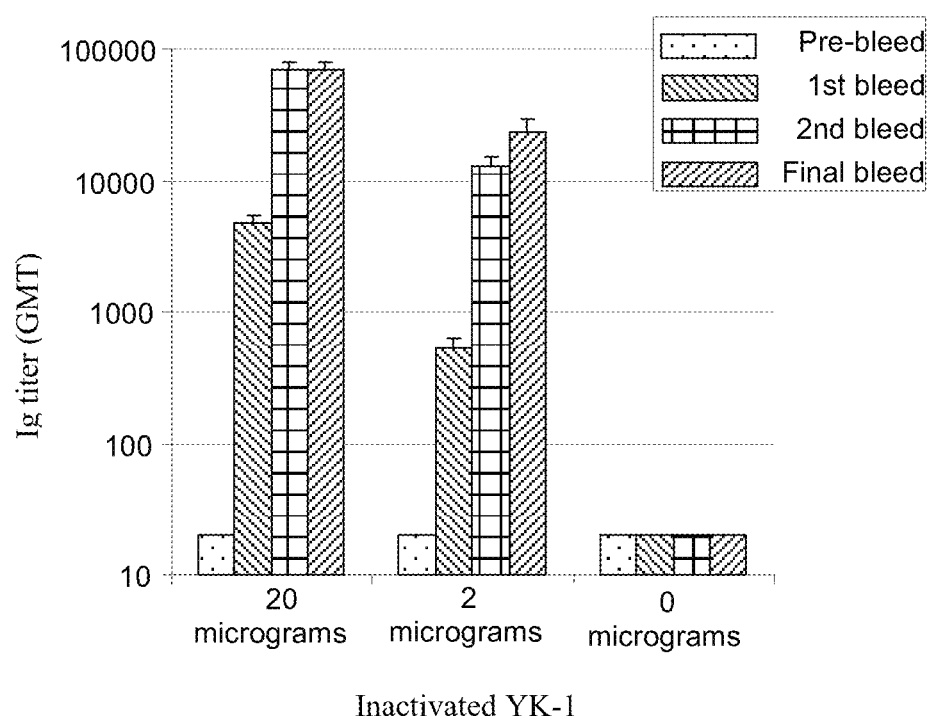
FIG. 3A is a graph showing total serum antibody response to thermally inactivated rotavirus.

FIG. 3A is a graph showing total serum antibody response to a composition including rotavirus thermally inactivated according to an embodiment of a method of the present invention. Antibody titer in FIG. 3A is expressed as the geometric mean for each group (n=7 or 6). The error bar represents 1 standard error. FIG. 3A illustrates that a rotavirus-specific total antibody response is observed in serum of mice which received one-dose immunization with 20 micrograms or 2 micrograms of thermally inactivated YK-1 rotavirus. Mice which received two immunizations with 20 micrograms of thermally inactivated rotavirus had high total antibody titers. Comparable though lower (2 to 8-fold) antibody titers are seen in mice that are inoculated twice with 2 micrograms of thermally inactivated rotavirus. These high levels of antibody are sustained 2 weeks later in the final serum specimens when the mice are euthanized. No antibody titers (<100) are detected in control mice that received diluent buffer.

Figure 3B:
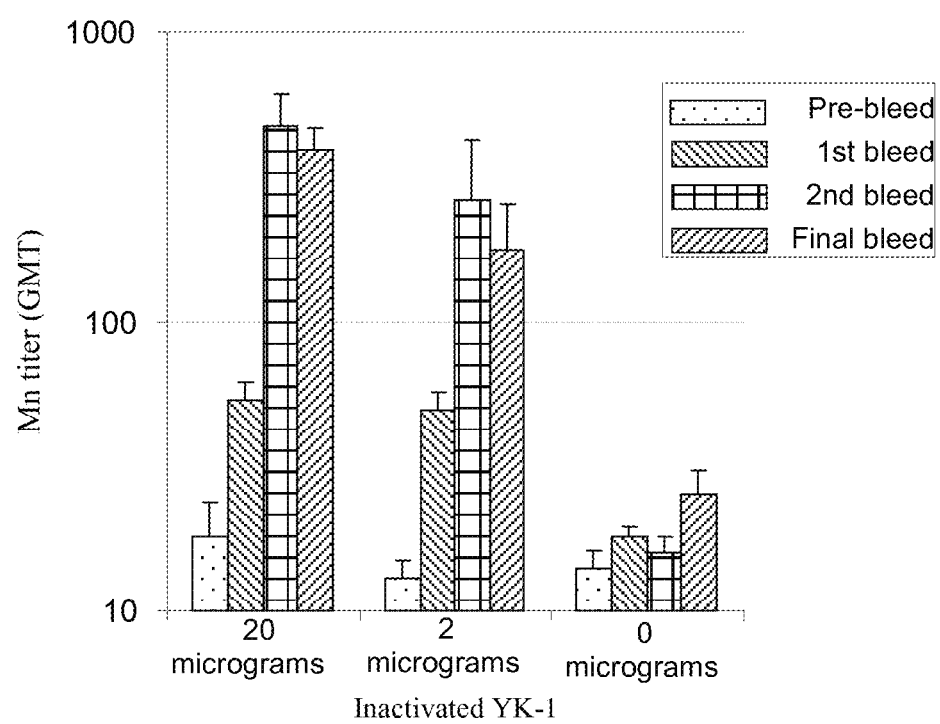
FIG. 3B is a graph showing neutralizing antibody response to thermally inactivated rotavirus.

Serum acquired from individual mice is tested for rotavirus-specific neutralizing antibody using a microneutralization assay and detected titers of neutralizing antibody with a pattern similar to that of total antibody response as shown in FIG. 3B. Antibody titer in FIG. 3B is expressed as the geometric mean for each group (n=7 or 6). The error bar represents 1 standard error. All but 2 pre-sera had a neutralization titer≤20 and the remaining two had a neutralization titer of 40. Mice in groups of 7 vaccinated once with 20 micrograms of thermally inactivated rotavirus or 2 micrograms of thermally inactivated rotavirus had a small rise (2 to 8 fold) in neutralizing antibody titer, which increased dramatically to up to 1280 following a second vaccination. Neutralizing antibody titers remained high 2 weeks later when the mice are euthanized. Mice immunized with diluent buffer had no rise in neutralization titers. Rotavirus-specific IgA is assayed in the same manner as total antibody and no rise in titer is detected in the sera of vaccinated mice.

Example 8

In particular trials, an AlOH adjuvant is added to compositions to enhance the immunogenicity of the heat inactivated rotavirus vaccine. In these trials, 30 BALB/C mice are divided into 5 groups of 6; mice in 4 groups are immunized I.M. once with 2 micrograms or 0.2 micrograms of antigen without or with 600 micrograms of AlOH. Control mice in group 5 are immunized with 600 micrograms of AlOH in the same manner Mice are bled on days 0 and 21, and exsanguinated on day 35. All sera are stored at −70° C. before being tested.

Neutralizing antibodies are determined by EIA. For total antibody, each serum specimen is tested at an initial dilution of 1:100. Pre-bleed serum specimens had no detectable antibody at this dilution, a value of 20 is used for determining geometric mean titers and illustration. Neutralizing antibody is tested at an initial dilution of 1:20. Results are shown in FIGS. 4A and 4B.

Figure 4A:
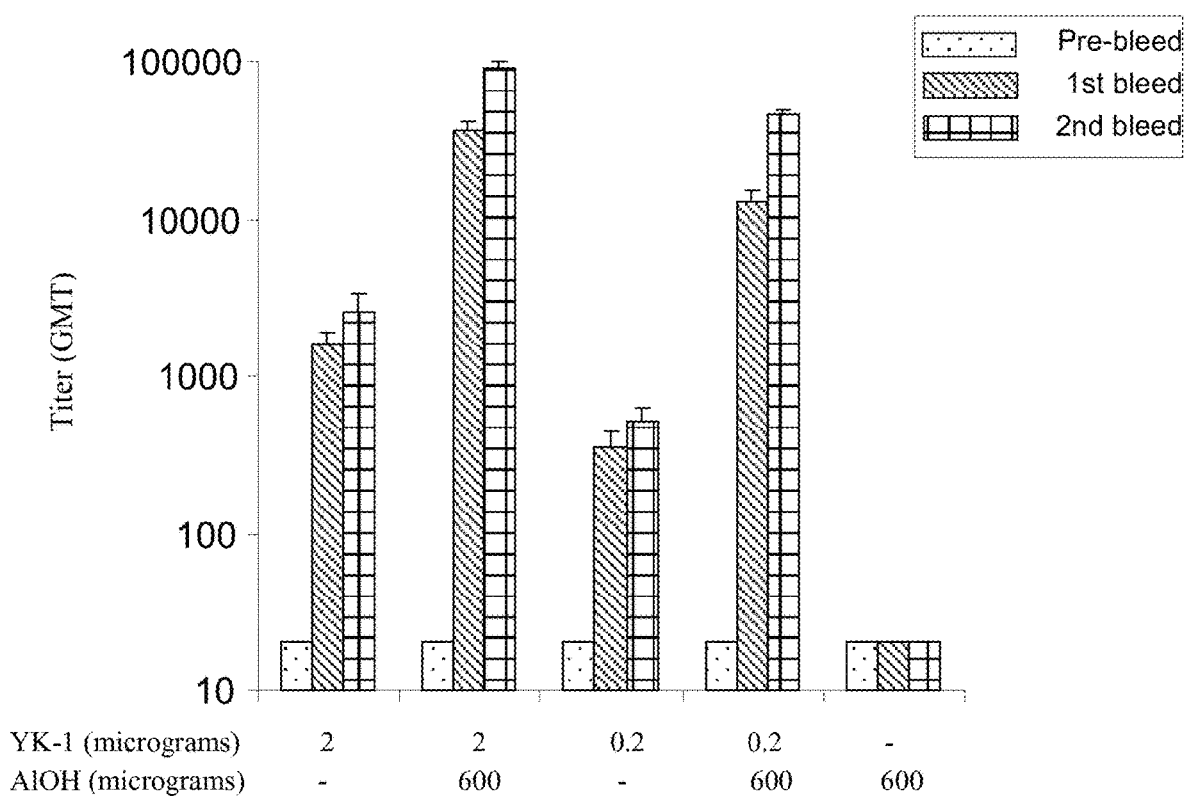
FIG. 4A is a graph showing total serum antibody response to a composition including AlOH and thermally inactivated rotavirus.

FIG. 4A is a graph showing total serum antibody response to a composition including AlOH and rotavirus thermally inactivated according to an embodiment of a method of the present invention. The addition of an adjuvant, AlOH, to the thermally inactivated YK-1 rotavirus enhances the immune response to the thermally inactivated YK-1 rotavirus and yields high titers of antibody with a very low dose of antigen as shown in FIGS. 4A and 4B. Antibody titers are expressed as the geometric means for each group (n=6) in FIGS. 4A and 4B. The error bars represent 1 standard error.

Mice in groups of 6 are immunized intramuscularly once with 2 micrograms or 0.2 micrograms of killed YK-1 without adjuvant or with 600 micrograms of AlOH. FIG. 4A shows that rotavirus-specific antibody titers are detected in mice that received 2 micrograms or 0.2 micrograms of antigens and that addition of AlOH to the vaccine enhances total antibody titers. These high antibody titers further increased 2 weeks later when the mice are euthanized Control mice that received 600 micrograms of AlOH had no rotavirus-specific antibody titers (<100).

Figure 4B:
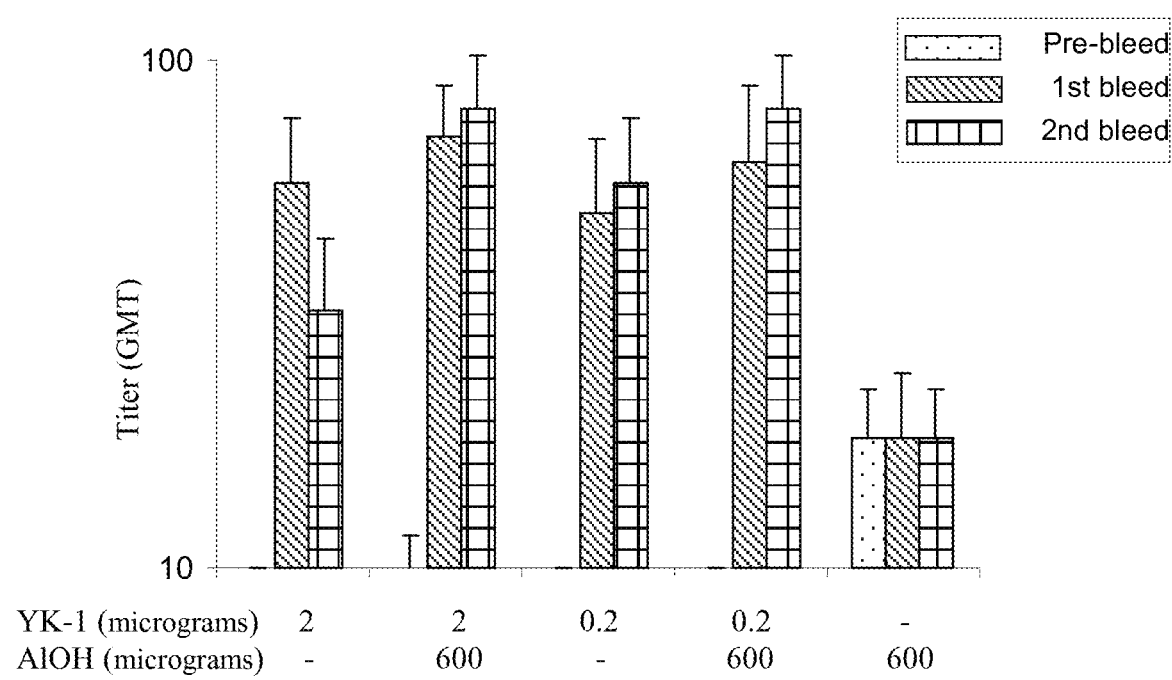
FIG. 4B is a graph showing neutralizing antibody response to a composition including AlOH and thermally inactivated rotavirus.

FIG. 4B is a graph showing neutralizing antibody response to a composition including AlOH and rotavirus thermally inactivated according to an embodiment of a method of the present invention.

Example 9

Purified human rotavirus A particles strain having a genotype P[8], G1 are resuspended in diluent buffer, Hank's Balanced Salt Solution (HBSS) with 1.3 mM $CaCl_2$, 0.5 mM $MgCl_2$, and 0.4 mM $MgSO_4$, supplemented with 10% sorbitol, and stored at −70° C. before being heat inactivated and injected into a subject.

A sample of the purified human rotavirus particles is diluted to a concentration of 300 micrograms/ml with diluent buffer, Hank's Balanced Salt Solution (HBSS) with 1.3 mM CaCl2, 0.5 mM $MgCl_2$, and 0.4 mM $MgSO_4$, supplemented with 10% sorbitol, and sterilized by filtration using a Millex-HV PVDF Syringe driven filter unit (0.45 micron; Millipore Corporation, Bedford, Mass.).

To inactivate the human rotavirus by heat, virus particles in diluent buffer are placed in 3.6 ml cryotubes (NalgeNunc, Rochester, N.Y.) are incubated for 1 hr at 60° C. in a waterbath with re-circulating water (model NesLab Ex10; Thermo Electron Corporation, Newington, N.H.) and then transferred to another fresh tube and incubated for an additional 1 hr at 60° C. A small aliquot is immediately tested for any residual infectivity and the remainder is stored at −70° C. before use in the immunization of a subject.

The effectiveness of inactivation is verified by inoculating thermally treated human rotavirus suspension onto monolayers of Vero cells in roller tubes and incubating in a rolling apparatus at 37° C. for 7 days. Infected cell cultures are then subjected to a second round of amplification in Vero cells in the same manner for another 7 days. Human rotavirus is considered inactivated if inoculated cell cultures tested negative for human rotavirus by using a commercial EIA kit (Rotaclone®; Meridian, Cincinnati, Ohio). In controls, non-heat treated human rotavirus is inoculated onto Vero cells in the same manner and infected cultures tested positive for human rotavirus.

The integrity of the rotavirus particles before and after thermal inactivation is determined by electron microscopy. Live and inactivated human rotavirus A particles are stained with phosphotungstic acid and examined with an electron microscope. After thermal treatment at 60° C. for 2 hrs, human rotavirus particles are found to maintain biophysical integrity, as evidenced by the preservation of triple-layered structures that are morphologically similar to live native virions. FIGS. 5A and 5B are reproductions of electron micrographs showing purified live and heat-killed (inactivated) human rotavirus A CDC-9.

Following heat inactivation, human rotavirus particles are examined by polyacrylamide gel electrophoresis and staining as well as by immunoassay to determine the protein content and integrity of the particles.

FIG. 6A is a reproduction of a digitized image of a Coomassie blue stained polyacrylamide gel showing molecular mass markers (kilodaltons) in lane 1, proteins from live human rotavirus in lanes 2 and 4 and proteins from thermally inactivated human rotavirus in lanes 3 and 5. Samples in lanes 2 and 3 were incubated at 37° C. for 10 min before analysis, whereas samples in lanes 4 and 5 were treated at 97° C. for 5 min before analysis.

FIG. 6B is a reproduction of a digitized image of an immunoblot showing mouse anti-rotavirus immunoreactive protein VP5 isolated from live human rotavirus in lane 2 and mouse anti-rotavirus immunoreactive proteins VP5 or its aggregates isolated from thermally inactivated human rotavirus in lane 3. Samples in lanes 2 and 3 were incubated at 37° C. for 10 min before analysis. No VP5 human rotavirus immunoreactive proteins or VP5 aggregates were detected in samples in lanes 4 and 5 that were treated at 97° C. for 5 min before analysis. The results show that heat inactivation does not destroy VP5 (a cleaved product of VP4) but may result in aggregates or rearrangements of VP5.

Figure 7:
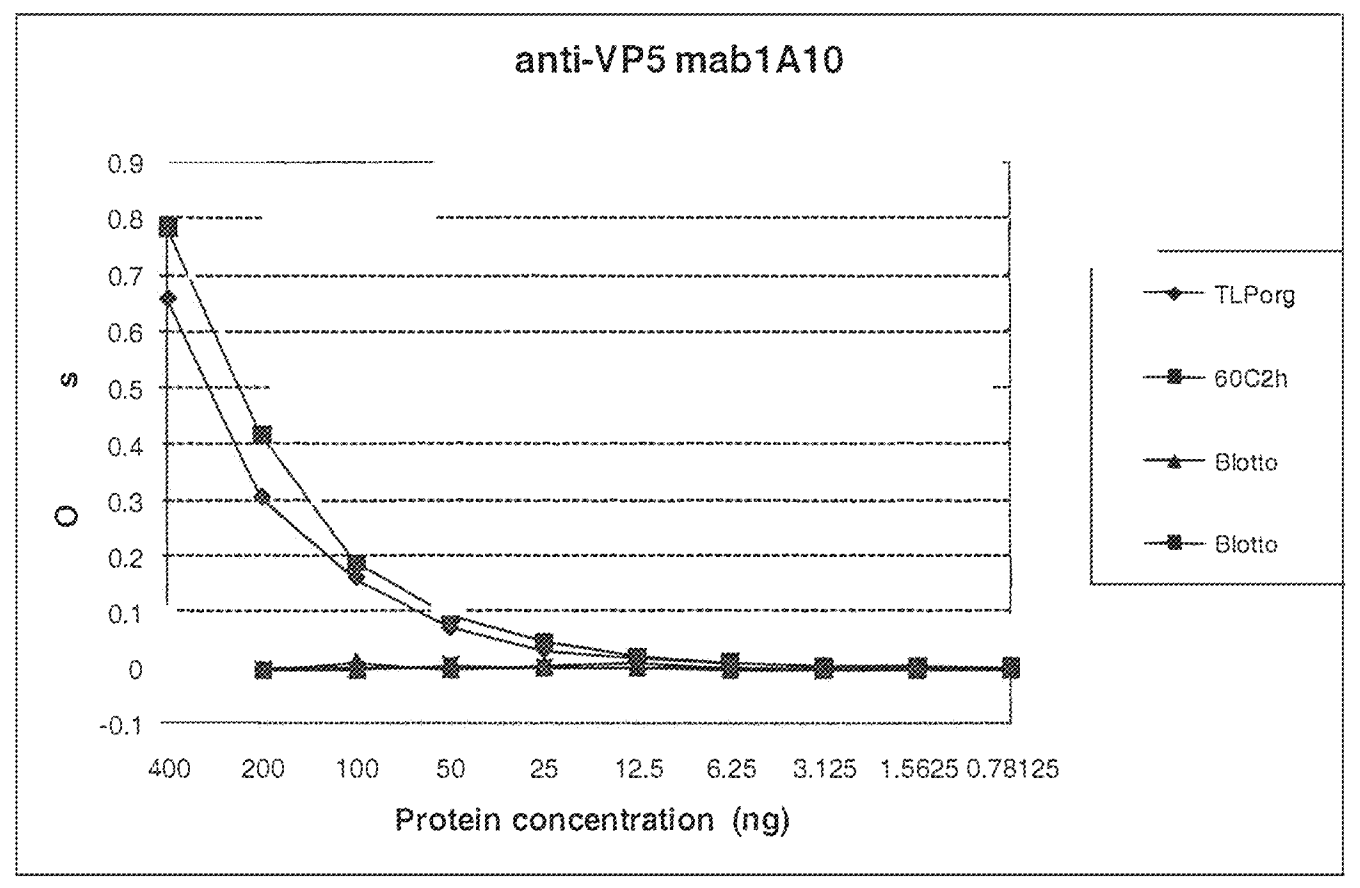

FIG. 7 is a graph showing analysis of human rotavirus CDC-9 by EIA using a VP5-specific monoclonal antibody. Similar levels of VP5 were detected in live and heat-inactivated CDC-9 preparations.

Example 10

Gnotobiotic Piglets—I

A gnotobiotic piglet model of rotavirus disease is used in particular examples. This piglet model allows testing under defined conditions avoiding problems of environment exposure of animals and using disease as the outcome variable. This model also allows testing of a heat-inactivated rotavirus vaccine having a G1 serotype against a homotypic Wa challenge.

Thirteen infant gnotobiotic piglets are selected and randomly assigned to 4 groups as indicated in Table 1.

TABLE 1

| Group Name | Number of Piglets in Group | CDC-9 Antigen (micrograms) | AlPO$_4$ (micrograms) |
|---|---|---|---|
| AA | 4 | 0 | 750 |
| BB | 4 | 75 | 0 |
| CC | 3 | 75 | 750 |
| DD | 2 | 0 (buffer) | 0 (buffer) |

Each group of animals indicated in Table 1 is kept in separate isolators. Animals in groups BB and CC are vaccinated intramuscularly 3 times with a heat-inactivated rotavirus vaccine without or with an adjuvant, respectively. The vaccine formulation in this example includes 75 micrograms of heat-killed purified CDC-9, a human rotavirus A strain having a serotype P[8], G1, in diluent mixed with 750 micrograms of AlPO$_4$. Animals in groups AA and DD are vaccinated with 750 micrograms of AlPO$_4$ and buffer, respectively, in the same manner Antigen adsorption is determined by the Bradford method which showed that about 50% of the antigen was bound to AlPO$_4$. Both bound and unbound antigen was injected in these immunizations.

Figure 8A:
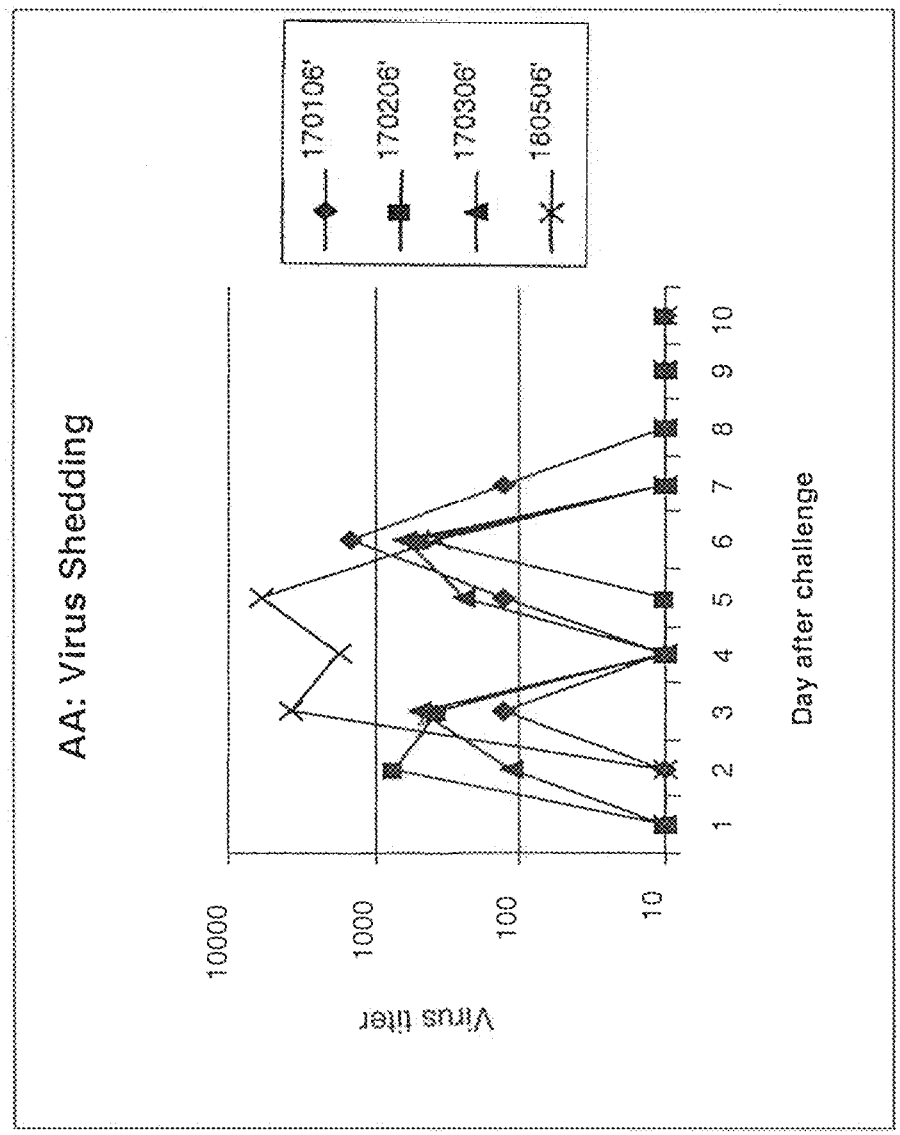
FIG. 8A is a graph showing virus shedding in fecal samples of piglets vaccinated with no antigen and with 750 micrograms of $AlPO_4$ in 4 animals.
Figure 8B:
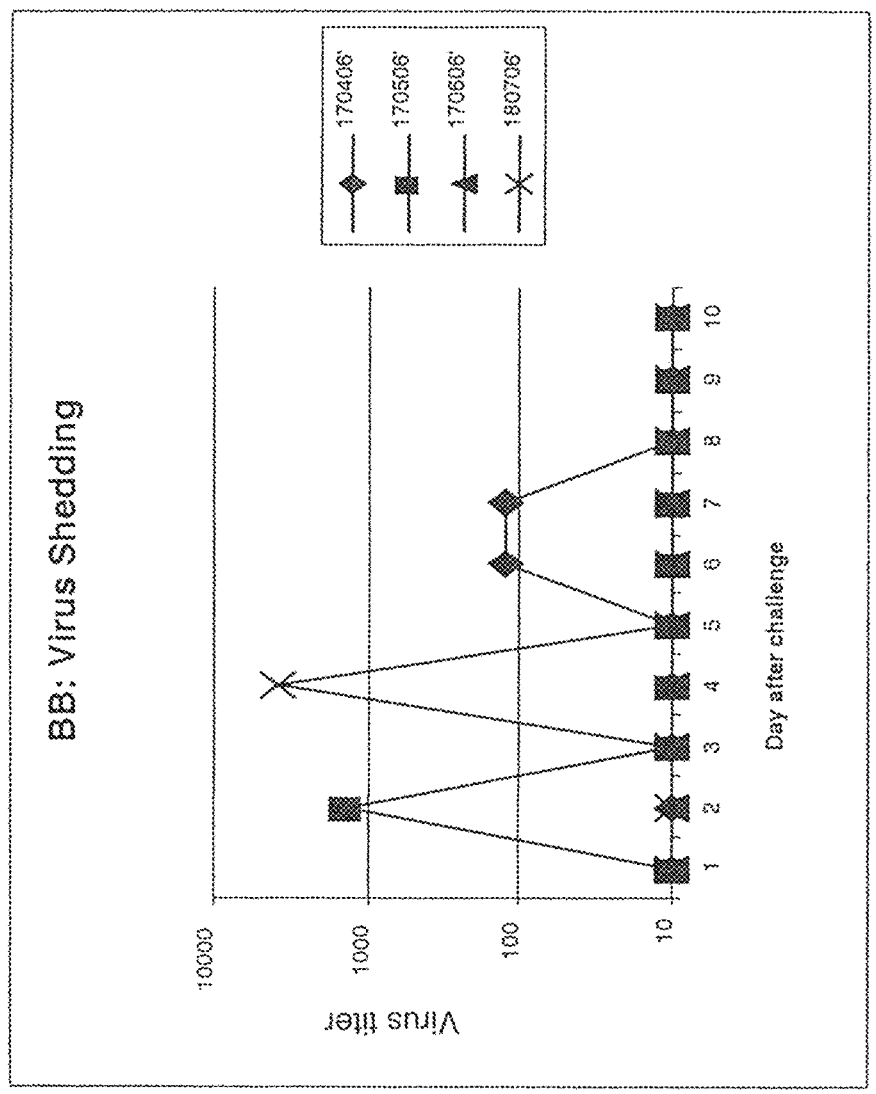
FIG. 8B is a graph showing virus shedding in fecal samples from piglets immunized with thermally-inactivated rotavirus and no adjuvant.
Figure 8C:
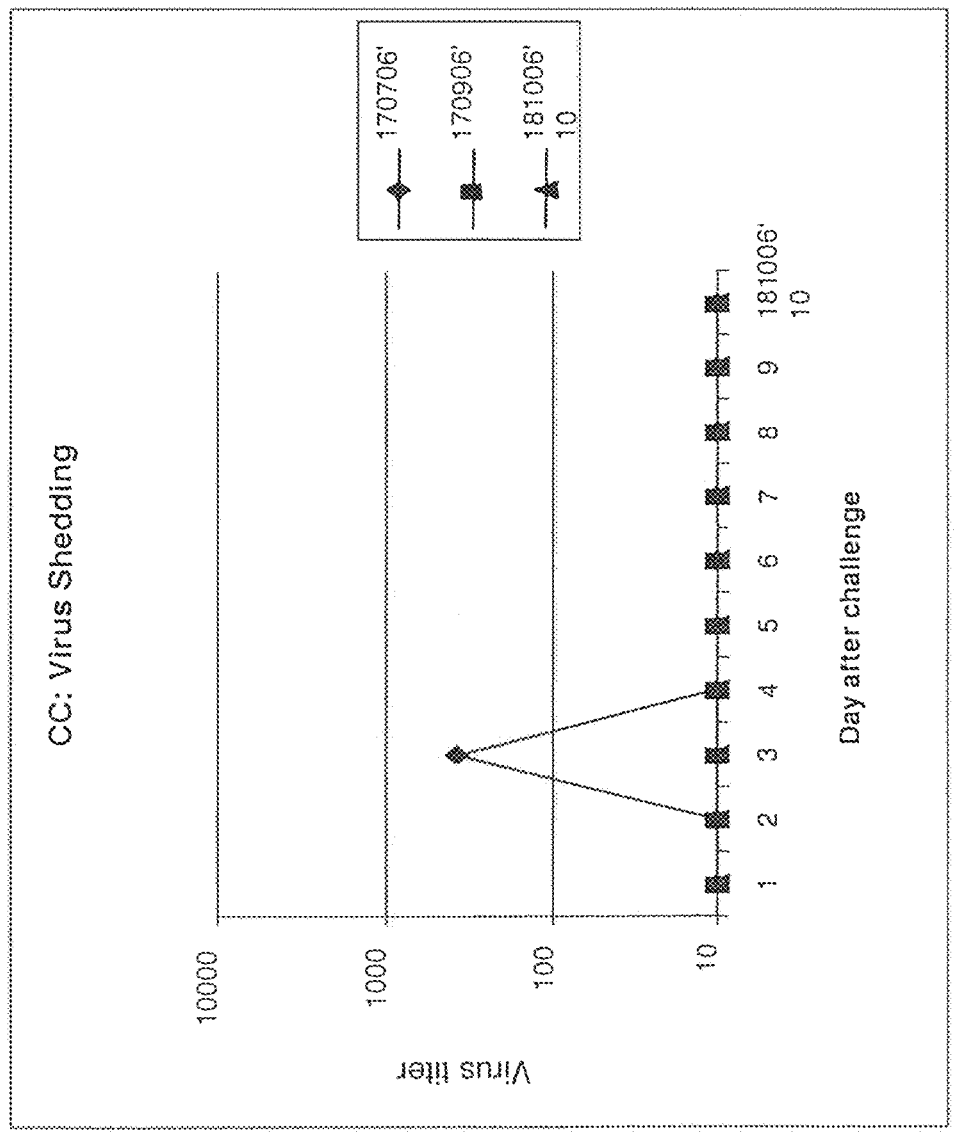
FIG. 8C is a graph showing virus shedding in fecal samples of piglets immunized with thermally-inactivated rotavirus and adjuvant.
Figure 8D:
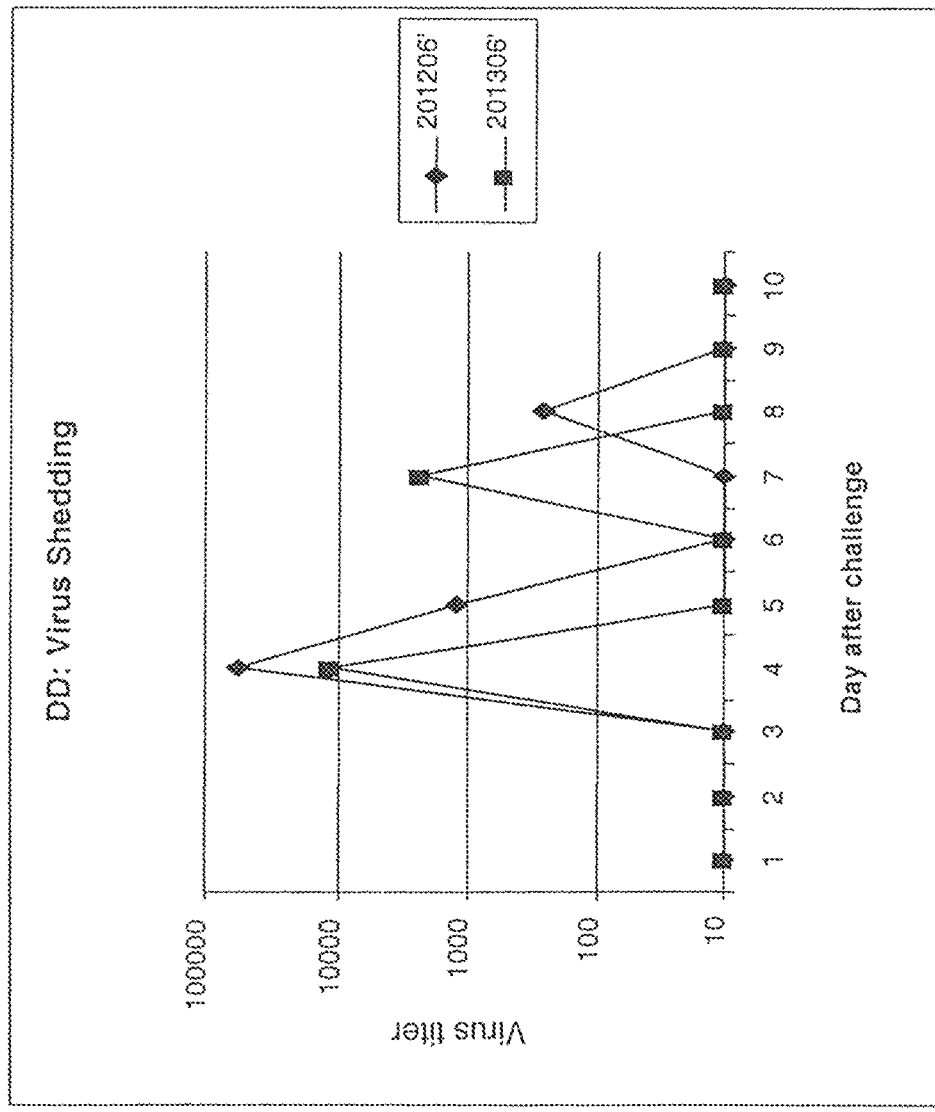
FIG. 8D is a graph showing virus shedding measured in fecal samples of piglets immunized with buffer only.

As shown in Table 1, piglets were immunized with a vaccine formulation including no antigen and 750 micrograms of AlPO$_4$; 75 micrograms of antigen and no AlPO$_4$; 75 micrograms of antigen and 750 micrograms of AlPO$_4$; or no antigen and no AlPO$_4$, that is buffer alone. Each vaccination was carried out by injecting 0.5 milliliters of the vaccine formulation into muscles of the hind legs of the piglets. After 3 doses of the vaccine formulation administered at intervals of 10-12 days, piglets were orally challenged with virulent Wa rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days. FIG. 8A shows virus shedding in fecal samples of piglets vaccinated with no antigen and with 750 micrograms of AlPO$_4$ in 4 animals. FIG. 8B shows virus shedding in fecal samples from piglets immunized with antigen and no adjuvant. FIG. 8C shows virus shedding in fecal samples of piglets immunized with antigen and adjuvant. FIG. 8D shows virus shedding measured in fecal samples of piglets immunized with buffer only. These figures show that piglets that were mock vaccinated with AlPO$_4$ only or diluent buffer only all shed rotavirus up to 5 days and at high titer. By contrast, piglets that were vaccinated with heat-inactivated rotavirus without AlPO$_4$ were partially protected, as evidenced by a shortened 1-day shedding or a delayed and reduced shedding. Of the 3 piglets that were vaccinated with heat-inactivated rotavirus and AlPO$_4$, 2 were completely protected and 1 had only a short, 1-day, reduced shedding. Thus these results show effectiveness of a heat-inactivated vaccine formulation according to embodiments of the present invention.

Example 11

Gnotobiotic Piglets—II

Eleven infant gnotobiotic piglets are selected and randomly assigned to 2 groups as indicated in Table 2.

TABLE 2

| Group Name | Number of Piglets in Group | CDC-9 Antigen (micrograms) | AlPO$_4$ (micrograms) |
|---|---|---|---|
| GG | 5 | 0 | 600 |
| HH | 6 | 50 | 600 |

As shown in Table 2, piglets were immunized with a vaccine formulation including no antigen and 600 micrograms of AlPO$_4$ or 50 micrograms of antigen and 600 micrograms of AlPO$_4$. Each vaccination was carried out by injecting 0.5 milliliters of the vaccine formulation into muscles of the hind legs of the piglets. After 3 doses of the vaccine formulation administered at intervals of 10-12 days, piglets were orally challenged with virulent Wa rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days.

Table 3 shows data indicating the neutralizing antibody titers in piglets that were vaccinated I.M. with heat-inactivated human rotavirus or placebo and orally challenged with human rotavirus Wa. Abbreviations used: ID, identification code; PID, post inoculation day; PCD, post challenge day; ND, not determined.

TABLE 3

| Group | Pig ID | PID 0 | PID 10 | PID 21 | PID 28 | PID42/PCD14 |
|---|---|---|---|---|---|---|
| GG | 13-7-07 | | ND | ND | 2 | 16.5 |
| | 13-8-07 | | ND | ND | 2 | 23.5 |

TABLE 3-continued

| Group | Pig ID | PID 0 | PID 10 | PID 21 | PID 28 | PID42/PCD14 |
|---|---|---|---|---|---|---|
|  | 13-9-07 |  | ND | ND | 2 | 22.5 |
|  | 13-10-07 |  | ND | ND | 2 | 175 |
|  | 13-11-07 |  | ND | ND | 2 | 19 |
|  | GMT |  | ND | ND | 2 | 31 |
| HH | 13-1-07 |  | 2 | 13 | 570 | 1750 |
|  | 13-2-07 |  | 2 | 4.8 | 500 | 3050 |
|  | 13-3-07 |  | 2 | 2 | 170 | 1450 |
|  | 13-4-07 |  | 2 | 4 | 270 | 4100 |
|  | 13-5-07 |  | 2 | 5.2 | 390 | 1350 |
|  | 13-6-07 |  | 2 | 5 | 405 | 3575 |
|  | GMT |  | 2 | 5 | 357 | 2313 |

Table 4 shows the antigen shedding profile in piglets that were vaccinated I.M. with heat-inactivated rotavirus (IRV) or placebo and orally challenged with human rotavirus Wa. Table 4 shows detection of human rotavirus antigen in fecal specimens collected from piglets 0 to 10 days after Wa challenge. Detection of human rotavirus antigen was measured by a commercial EIA kit (Rotaclone). Shown are OD values. Abbreviations used: PID. The data show that administration of heat inactivated human rotavirus reduces the magnitude and duration of rotavirus shedding.

TABLE 4

| Group | Pig ID | PID |  |  |  |  |  |  |  |  |  |  |
|---|---|---|---|---|---|---|---|---|---|---|---|---|
|  |  | 0 | 1 | 2 | 3 | 4 | 5 | 6 | 7 | 8 | 9 | 10 |
| HH | 13-1 | 0 | 0 | 0 | 0 | 1 | 0 | 0 | 0 | 0 | 0 | 0 |
|  | 13-2 | 0 | 0 | 0 | 0 | 0 | 0 | 0 | 0 | 0 | 0 | 0 |
|  | 13-3 | 0 | 0 | 0 | 0 | 1 | 0 | 0 | 0 | 0 | 0 | 0 |
|  | 13-4 | 0 | 0 | 0 | 0 | 4 | 0 | 0 | 0 | 0 | 0 | 0 |
|  | 13-5 | 0 | 0 | 0 | 0 | 0 | 0 | 0 | 0 | 0 | 0 | 0 |
|  | 13-6 | 0 | 0 | 0 | 0 | 0 | 0 | 0 | 0 | 0 | 0 | 0 |
| GG | 13-7 | 0 | 0 | 0 | 0 | 32 | 8 | 1 | 0 | 0 | 0 | 0 |
|  | 13-8 | 0 | 0 | 1 | 0.1 | 4 | 4 | 1 | 0 | 0 | 0 | 0 |
|  | 13-9 | 0 | 0 | 0 | 0 | 8 | 2 | 0 | 0 | 0 | 0 | 0 |
|  | 13-10 | 0 | 0 | 8 | 0.1 | 8 | 4 | 0 | 0 | 0 | 0 | 0 |
|  | 13-11 | 0 | 0 | 0 | 0 | 2 | 16 | 4 | 0 | 0 | 0 | 0 |

Figure 9:
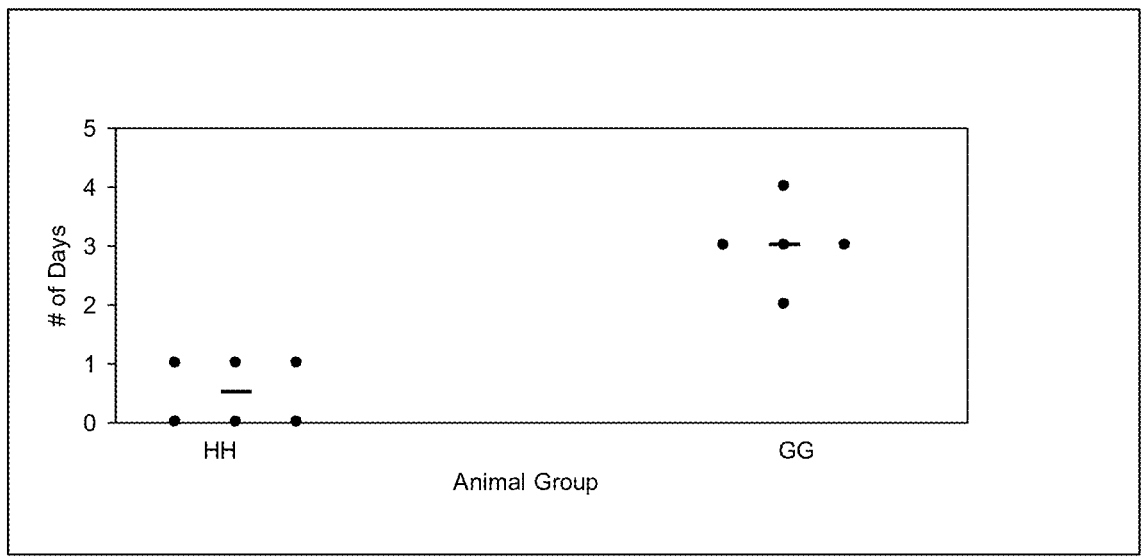
FIG. 9 is a graph showing a reduced number of days of rotavirus shedding in subjects vaccinated with heat-inactivated rotavirus (HH) compared to placebo controls (GG).

FIG. 9 is a graph showing that piglets vaccinated with thermally inactivated rotavirus have reduced duration of rotavirus shedding in fecal specimens collected from piglets after Wa rotavirus challenge. Detection of human rotavirus antigen was measured by a commercial EIA kit (Rotaclone). The data show that vaccination with thermally inactivated rotavirus is protective against infection.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

We claim:

1. A method of inducing an immune response to rotavirus in a subject, comprising:
   administering to the subject a therapeutically effective amount of a vaccine composition, wherein the vaccine composition comprises:
   a) an antigenic thermally-inactivated rotavirus that has a substantially intact rotavirus particle structure, wherein the substantially intact rotavirus particle structure is triple-layer rotavirus particles, double-layer rotavirus particles, or a combination of triple-layer rotavirus particles and double-layer rotavirus particles, and wherein the antigenic thermally-inactivated rotavirus is produced by the process of
   suspending isolated rotavirus particles in an aqueous buffer, the aqueous buffer having an osmolality in the range of about 200-500 mOsm, comprising a concentration of a salt of a divalent cation in the range of about 1 mM-15 mM and an amount of a sugar and/or sugar alcohol in the range of about 1-20% w/v to produce a starting preparation of rotavirus particles having an intact rotavirus particle structure;
   exposing the starting preparation of rotavirus particles to a temperature in the range of about 50° C.-73° C., inclusive, for an incubation time sufficient to render the rotavirus incapable of replication or infection, wherein the incubation time is in the range of about 30 minutes to 24 hours inclusive, thereby producing the thermally-inactivated rotavirus;
   b) an adjuvant; and
   c) a sterile pharmaceutically acceptable carrier,
   thereby inducing the immune response to the rotavirus in the subject.

2. The method of inducing an immune response to rotavirus of claim 1, wherein the subject is human.

3. The method of inducing an immune response to rotavirus of claim 1, wherein the vaccine composition is administered to the subject by a parenteral route.

4. The method of inducing an immune response to of claim 1, wherein administering the vaccine composition comprises administering at least two doses of the vaccine composition.

5. The method of claim 1, wherein the subject has a rotavirus infection.

6. The method of claim 5, wherein the method reduces the amount of virus shed in feces, reduces the number of days in which the virus is shed in feces, or reduces a symptom of the rotavirus infection.

7. The method of claim 1, wherein the immune response comprises the production of neutralizing antibodies for the rotavirus.

8. The method of claim 1, wherein the antigenic thermally inactivated rotavirus comprises a viral protein (VP)1, VP2 and VP6 that are substantially intact as compared to the rotavirus particles.

9. The method of claim 1, wherein the rotavirus is a group A, group B or group C rotavirus.

10. The method of claim 1, wherein the rotavirus is an animal rotavirus.

11. The method of claim 2, wherein the rotavirus is a human rotavirus.

12. The method of claim 1, wherein exposing the starting preparation of rotavirus particle to a temperature in the range of about 50° C. to 73° C., inclusive comprises a first incubation period and a second incubation period, wherein the first incubation period and the second incubation period combined are in the range of about 30 minutes to 24 hours, inclusive.

13. The method of claim 1, wherein the adjuvant comprises an AlOH, an AlPO$_4$, an aluminum oxide, or an aluminum salt.

14. The method of claim 13, wherein the adjuvant is AlOH.

15. The method of claim 13, wherein the adjuvant is AlPO$_4$.

16. The method of claim 1, wherein the adjuvant is Freund's adjuvant, iron oxide, saponin, DEAE-dextran, mineral oil, or a bacterial lipopolysaccharide.

17. The method of claim 1, wherein the rotavirus is a P[8], G1 rotavirus.

* * * * *

UNITED STATES PATENT AND TRADEMARK OFFICE
CERTIFICATE OF CORRECTION

PATENT NO. : 10,556,001 B2
APPLICATION NO. : 15/725221
DATED : February 11, 2020
INVENTOR(S) : Jiang et al.

Page 1 of 1

It is certified that error appears in the above-identified patent and that said Letters Patent is hereby corrected as shown below:

In the Claims

In Column 18, Line 31, Claim 4, "The method of inducing an immune response to of claim 1" should read --The method of inducing an immune response to rotavirus of claim 1--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*